United States Patent [19]

Syrinek

[11] Patent Number: 5,444,088
[45] Date of Patent: Aug. 22, 1995

[54] SYNERGISTIC ANTI-MICROBIAL COMPOSITIONS COMPRISING 2-BROMO-2-(BROMOMETHYL)-GLUTARONITRILE AND 2-BROMO-2-NITRO-PROPANE-1,3-DIOL

[75] Inventor: Allen R. Syrinek, Richmond, Tex.

[73] Assignee: Nalco Chemical Company, Naperville, Ill.

[21] Appl. No.: 131,883

[22] Filed: Oct. 5, 1993

[51] Int. Cl.$^6$ .................. A01N 33/18; A01N 33/24; A01N 37/34
[52] U.S. Cl. .................. 514/526; 106/18.32; 514/727; 523/122
[58] Field of Search .................. 514/526, 727; 106/18.32; 523/122

[56] References Cited

U.S. PATENT DOCUMENTS 4,604,405  8/1986  Jakubowski .................. 514/526
4,655,815  4/1987  Jakubowski .................. 71/67
5,304,567  4/1994  Hsu .................. 514/372

*Primary Examiner*—Allen J. Robinson
*Attorney, Agent, or Firm*—Robert A. Miller; James J. Drake

[57] ABSTRACT

This invention relates to methods and compositions for obtaining synergistic anti-microbial (biocidal) activity using a combination of 2-bromo-2-(bromomethyl)-glutaronitrile and 2-bromo-2-nitro-propane-1,3-diol. The methods and compositions of the invention are very effective in preventing microbial spoilage of latex carpet backing compounds and in paper and pulp preparation, particularly with respect to latex paper coatings. Compositions containing the active ingredients in ratios of from 0.0015 parts 2-bromo-2-(bromomethyl)-glutaronitrile to 1 part 2-bromo-2-nitro-propane-1,3-diol to 40 parts 2-bromo-2-(bromomethyl)-glutaronitrile to 1 part 2-bromo-2-nitro-propane-1,3-diol.

15 Claims, 4 Drawing Sheets

FIG.1

|  | 0 | 2 (.5) | 4 (1) | 8 (2) | 16 (4) | 32 (8) | 64 (16) | 125 (31.25) | 250 (62.5) | 500 (125) | Contaminated Latex Dilutions | Tektomer 38 alone |
|---|---|---|---|---|---|---|---|---|---|---|---|---|
| A 125 (1.25) | | | | | | | | | | | | |
| B 64 (26.24) | | | | | | | | | | | | |
| C 32 (13.1) | MIC 6.56 ppm BNPD | | | | | | | | | | | MIC 6.25 ppm BBMG |
| D 16 (6.56) | | | | | | | | | | | | |
| E 8 (3.28) | | | | | | | | | | | | |
| F 4 (1.64) | | | | | | | | | | | | |
| G 2 (.82) | | | | | | | | | | | | |
| H 1 (.41) | | | | | | | | | | | | |

NALCO Nalco 5780 (BNPD ppm)

Column

FIG. 2

| | 1 | 2 | 3 | 4 | 5 | 6 | 7 | 8 | 9 | 10 | 11 | 12 | Row |
|---|---|---|---|---|---|---|---|---|---|---|---|---|---|
| 125 (1.25) | | | | | | | | | | | | | A |
| 64 (26.24) | | | | | | | | | | | ░ | | B |
| 32 (13.1) | | | | | | | | | | | ░ | | C |
| NALCO 16 (6.56) | | | | | | | | | | | | | D |
| Nalco 5780 8 (3.28) | | | | | | | | | | | | | E |
| (BNPD ppm) 4 (1.64) | | ░ | | | | | | | | | | | F |
| 2 (.82) | ░ | ░ | ░ | | | | | | | | | | G |
| 1 (.41) | ░ | | | ░ | | | | | | | | ░ | H |
| | 0 | 4 (1) | 8 (2) | 16 (4) | 32 (8) | 64 (16) | 125 (31.25) | 250 (62.5) | 500 (125) | 1000 (250) | Contaminated Latex Alone | Tektamer 38 alone | |

MIC 1.64 ppm BNPD (column 1, row G)

MIC 8 ppm BBMG (column 3, row G; column 12, row H)

Column

FIG. 3

|  | 0 | 4 (1) | 8 (2) | 16 (4) | 32 (8) | 64 (16) | 125 (31.25) | 250 (62.5) | 500 (125) | 1000 (250) | Contaminated Latex Alone | Tektamer 38 alone |
|---|---|---|---|---|---|---|---|---|---|---|---|---|
| A 125 (1.25) |  |  |  |  |  |  |  |  |  |  |  |  |
| B 64 (26.24) |  |  |  |  |  |  |  |  |  |  |  |  |
| C 32 (13.1) |  |  |  |  |  |  |  |  |  |  |  |  |
| D 16 (6.56) NALCO |  |  |  |  |  |  |  |  |  |  |  |  |
| E 8 (3.28) Nalco 5780 | MIC 6.56 ppm BNPD |  |  |  |  |  |  |  |  |  |  | MIC 31.25 ppm BBMG |
| F 4 (1.64) (BNPD ppm) |  |  |  |  |  |  |  |  |  |  |  |  |
| G 2 (.82) |  |  |  |  |  |  |  |  |  |  |  |  |
| H 1 (.41) |  |  |  |  |  |  |  |  |  |  |  |  |
|  | 1 | 2 | 3 | 4 | 5 | 6 | 7 | 8 | 9 | 10 | 11 | 12 |

Column

FIG. 4

SYNERGISTIC ANTI-MICROBIAL COMPOSITIONS COMPRISING 2-BROMO-2-(BROMOMETHYL)-GLUTARONITRILE AND 2-BROMO-2-NITRO-PROPANE-1,3-DIOL

FIELD OF THE INVENTION

This invention relates to methods and compositions for obtaining synergistic anti-microbial (biocidal) activity using a combination of 2-bromo-2-(bromomethyl)-glutaronitrile and 2-bromo-2-nitro-propane-1,3-diol. The methods and compositions of the invention are very effective in preventing microbial spoilage of latex carpet backing compounds and in paper and pulp preparation, particularly with respect to latex paper coatings.

BACKGROUND OF THE INVENTION

Styrene/butadiene rubber latexes are used in adhesives for carpet backing to prevent the unraveling of the carpet fibers and are also used in the paper industry as coatings. One of the problems associated with the latexes is microbial (particularly bacterial) contamination of the uncured latex. Several problems ensue when formulated latex coatings, adhesives, or backings become contaminated. These include an offensive odor, which remains in the latex after it is cured and renders the resulting carpet or other product undesirable for use, changes in rheology of the adhesive or backing, which prohibit uniform coating of a carpet-back surface and make the viscosity of the adhesive or backing unsuitable for use, and reduced surface properties, which cause an adhesive or backing to lose strength and which can result in delamination of a carpet from its backing.

Contamination is most often noticed first by odor. When the microbial count exceeds 100,000 microbes per ml, odor begins to become apparent. The offending microbes can include bacteria, fungi (and yeasts), algae and other microscopic forms of life. Although yeasts and fungi can present problems, most problems in the spoilage of carpet backing compounds are caused by bacteria. Gram-negative bacteria are of particular importance in this regard as they are generally viewed as causing more degradation than gram-positive bacteria. For example, *Pseudomonas aeruginosa*, which is widely distributed in nature and is found in the water, soil, and intestinal tract of man and animals and consequently, is a commonly occurring bacterial contaminant. See "Test Method D4783-89" published by the American Society for Testing and Materials for further information concerning common contaminants.

Contamination of latex backing or adhesive can have several sources. The first source may be the finished latex itself. If the latex is not properly treated, it may introduce contaminants into the carpet mill where it is formulated. The scrim adhesive-type latexes used in carpet backcoatings are all carboxylated; the foam backing types (cold polymerized SBR latex) are not. In some cases, contamination results from shipping or extensive storage of finished latex.

The second source of potential problems is the raw materials used with finished latex. Typically, the styrene-butadiene latex backcoatings are heavily filled with calcium carbonate or clay, which are sources of microbial contamination. Unsterilized water has also been used as dilution, washing or carrying agent. Many times recycled water is used for dilution of latex. The industry is moving towards recycling water because of environmental, safety and economic concerns, and the recycled water presents an ideal environment for microbial growth. Commonly added defoamers, surfactants and viscosifiers could also be bacteria carriers.

Another source of potential problems is the storage of compounded latex. Storage of the compounded latex in storage tanks where temperature and time of storage are not strictly controlled all pose opportunities for introduction and growth of bacteria.

In the past, latex suppliers have added microbicide to the latex to control contamination in the carpet mills. Such microbicides include for example, 1,2-benzoisothiazolin-3-one, which is sold by Imperial Chemical Industries under the trade name Proxel GXL, and a mix of 5-chloro-2-methyl-4-isothiazolin-3one and 2-methyl-4-isothiazolin-3-one, which is sold by Rohm and Haas under the trade name Kathlon LX, and a mix of 1,2-dibromo-2,4-dicyanobutane and 1,2-benzoisothiazolin-3-one, which is sold by Calgon under the trade name Biocheck 410. However, these products suffer from certain shortcomings. For example, high concentrations of 1,2-benzoisothiazolin-3-one, are required to adequately preserve the latex.

Tetrahydro-3,5-dimethyl-2H-1,3,5-thiadiazine-2-thione (Nalco 5787) and Nalco 5793 have also been used in carpet backing adhesives. Nalco 5787 is a preservative at high dosages but has odor problems and does not offer quick kill capabilities. Nalco 5793 is a good quick kill biocide but does not offer preservation. Therefore, it is apparent that an improved method and composition for inhibiting growth of microorganisms (and bacteria in particular) in latex backing formulations is needed.

Co-pending application No. 08/088,050, filed Jul. 7, 1993, now U.S. Pat. No. 5,385,605, (and incorporated herein by reference) discloses a synergistic composition comprising methylene(bisthiocyanate) and 2-bromo-2-nitro-propane 1,3-diol. The inventor has now discovered that compositions containing 2-bromo-2-(bromomethyl)-glutaronitrile and 2-bromo-2-nitro-propane 1,3-diol are also synergistic.

SUMMARY OF THE INVENTION

This invention provides a surprisingly efficacious combination useful for inhibiting microorganism growth, particularly in compositions containing latex, e.g., for use in carpet manufacture.

In particular embodiments the invention provides an anti-microbial composition comprising 2-bromo-2-(bromomethyl)-glutaronitrile and 2-bromo-2-nitro-propane-1,3-diol in a ratio ranging from about 0.015 parts 2-bromo-2-(bromomethyl)glutaronitrile to 1 part 2-bromo-2-nitro-propane-1,3-diol to about 40 parts 2-bromo-2-(bromomethyl)-glutaronitrile to 1 part 2-bromo-2-nitro-propane-1,3-diol. In one embodiment, the composition contains at least 0.5 parts per million 2-bromo-2-(bromomethyl)-glutaronitrile and at least 1.64 parts per million 2-bromo-2-nitro-propane-1,3-diol, and, in a second embodiment, at least 4 parts per million 2-bromo-2-(bromomethyl)-glutaronitrile and at least 0.82 parts per million 2-bromo-2-nitro-propane-1,3diol. More preferably, the composition contains at least 16 parts per million 2-bromo-2-(bromomethyl)-glutaronitrile and at least 3 parts per million 2-bromo-2-nitro-propane-1,3-diol. An anti-microbial formulation comprising 0.25 parts to 64 parts (more preferably from about 2 parts to about 8 parts) of a dispersion containing about 25% 2-bromo-2-(bromomethyl)-glutaronitrile as the active ingredient to about one part of an aqueous solution containing about 41% 2-bromo-2-nitro-propane-1,3-diol is also included. The ratio of the dispersion to the aqueous solution may also be four parts to one part. Tektamer 38, Calgon Corp., Pittsburgh, Pa., may be used as the dispersion and Nalco 5780 may be used as the solution.

The invention also provides a method for inhibiting microbial growth in a composition that contains a latex. The method includes the step of adding to the composition 2-bromo-2-(bromomethyl)-glutaronitrile and 2-bromo-2-nitro-propane-1,3-diol in a ratio ranging from 0.15 parts 2-bromo-2-(bromomethyl)glutaronitrile to 1 part 2-bromo-2-nitro-propane-1,3-diol to 40 parts 2-bromo-2-(bromomethyl)-glutaronitrile to 1 part 2-bromo-2-nitro-propane-1,3-diol, in amounts of each which in combination, are effective to inhibit microbial growth. In one embodiment, the amount of 2-bromo-2-(bromomethyl)-glutaronitrile is at least 0.5 parts per million and the amount of 2-bromo-2-nitro-propane-1,3-diol is at least 1.64 parts per million. In another embodiment, the amount of 2-bromo-2-(bromomethyl)-glutaronitrile is at least 4 parts per million and the amount of 2-bromo-2-nitro-propane-1,3-diol is at least 0.82 parts per million, and in adapted for handling higher contamination levels, the amount of 2-bromo-2-(bromomethyl)-glutaronitrile is at least 16 parts per million and the amount of 2-bromo-2-nitro-propane-1,3-diol is at least 3 parts per million. Among other things, the methods of the invention may be used to treat uncured latex compounds formulated for use as a carpet backing or adhesive or for use as a paper coating. A composition for use as a carpet backing comprising latex, water, a filling agent (such as ground limestone or calcium carbonate), and 2-bromo-2-(bromomethyl)-glutaronitrile and 2-bromo-2-nitro-propane-1,3-diol in amounts of each that, in combination, are effective to inhibit microbial growth in the latex is also claimed.

DESCRIPTION OF THE DRAWINGS

FIG. 1 representation of a microtiter plates in which a combination of Tektamer 38 and Nalco 5780 showed synergistic biocidal activity against a culture of wild bacteria in latex-containing medium. Shaded squares represent wells of the plate in which bacterial contamination was detected by a change of color (from dark purple to bright pink) in the culture medium.

FIGS. 2 and 3 are representations of microtiter plates in which Tektamer 38 and Nalco 5780 showed synergistic activity against a culture of Pseudomonas aeruginosa in a latex containing medium. Shaded squares represent wells of the plate in which bacterial contamination was detected by a change of color (from dark purple to bright pink) in the culture medium.

Figure 4:
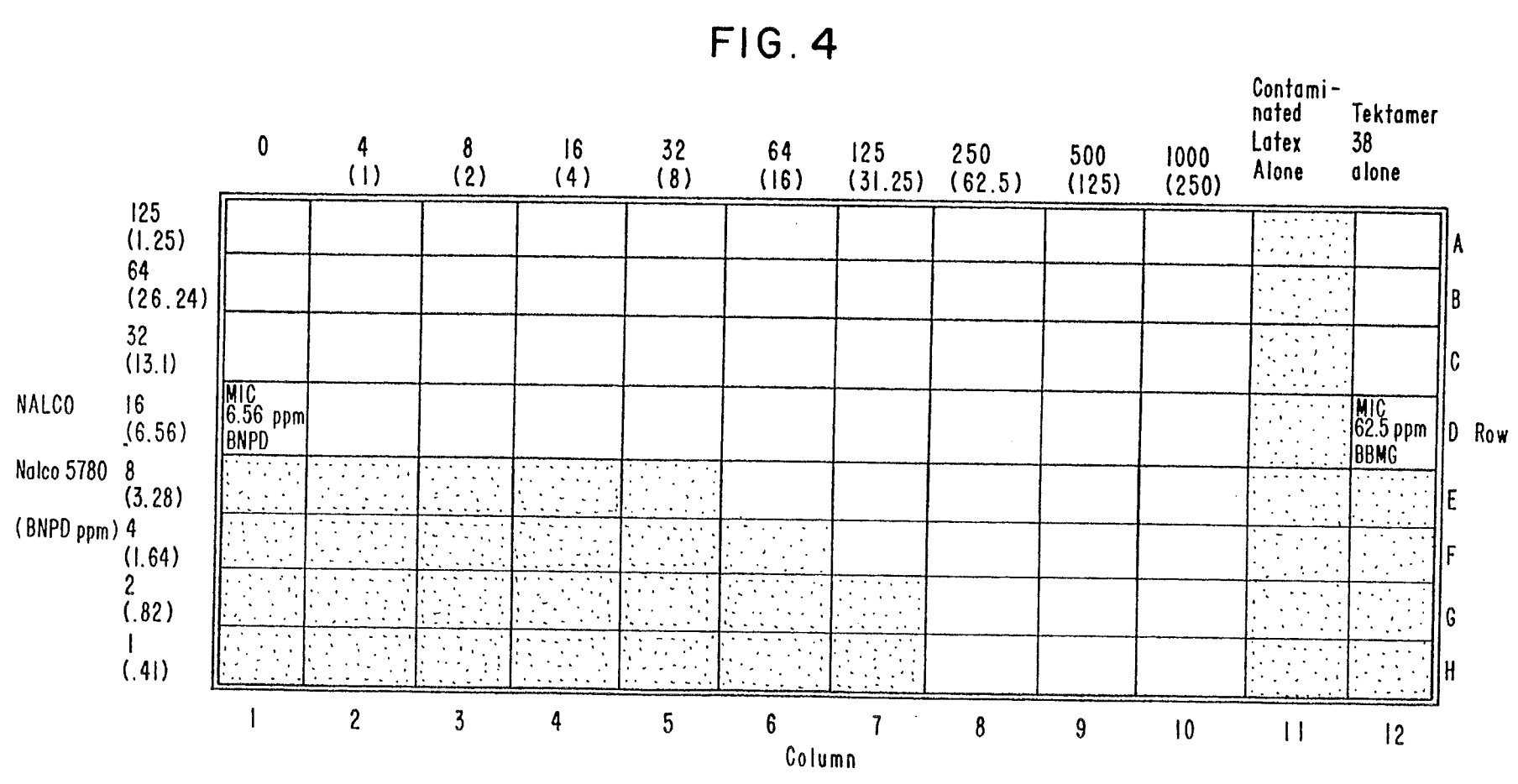

FIG. 4 is a representation of a microtiter plate in which Tektamer 38 and Nalco 5780 showed synergistic activity against a wild culture in a latex containing medium. Shaded squares represent wells of the plate in which bacterial contamination was detected by a change of color (from dark purple to bright pink) in the culture medium.

DETAILED DESCRIPTION OF THE INVENTION

The synergistic anti-microbial composition of the present invention may find utility in a variety of applications in which biocides are commonly used including, e.g., applications in industries that make or use paper, wood and pulp and their products and in the latex industry, e.g., in preparation of paints and other coatings. However, a particularly important contribution of the synergistic anti-microbial composition is to the carpet industry, to prevent purification of latex carpet backing. Accordingly, without limiting the invention in any way, the use of the synergistic anti-microbials of the present invention in this context is described below.

In a preferred embodiment, a synergistic combination of 2-bromo-2-(bromomethyl)-glutaronitrile ("BBMG") and 2-bromo-2-nitro-propane-1,3-diol ("BNPD") is used for protection of a latex adhesive or backing formulated for use with a carpet or carpet tile product. The combination of these agents may be used in protection of any of a number of latex-adhesive formulations used in the carpet industry. Examples of polymers and copolymers that may be used in the latex base include, for example, vinyl acetate-ethylene, styrene-butadiene, vinylidene chloride, vinyl chloride, cellulose acetate butyrate, vinyl chlorideacrylonitrile, vinyl acetate-acrylic acid, vinylidene-chlorideacrylonitrile, acrylic acid-methacrylic acid, butadieneacrylonitrile, acrylic acid-styrene, acrylonitrile-styrene, acrylonitrile-acrylic acid, acrylonitrile-alkyl acrylate, vinyl acetate acrylate ester, acrylonitrile butadiene styrene and others.

The active agents can be added directly to the latex base used to formulate the compounded latex adhesive or backing. In addition, the compounds can be added to the latex mixture at any of a number of points in the production process, e.g., in line as the mixture delivered to the tank for compounding, in the compounding chamber, in line as the mixture is delivered from the compounding chamber to a storage tank, or in the storage tank itself. Preferably, the agents are added before latex is cured, and more preferably before compounded latex is applied to the carpet, since microbial contamination usually occurs prior to this step. In some embodiments, each of the synergistic agents is added separately and is allowed to mix with the latex at the point of addition or thereafter. Alternatively, the synergistic agents may be formulated together and added as a single ingredient at any of the points described above.

The synergistic combination of BBMG and BNPD has been shown to be effective over a wide range of concentrations and compound ratios. In general, however, it is preferred to add the components in an amount sufficient to produce final concentrations in the compounded latex ranging from at least about 0.5 ppm BBMG and more preferably from at least about 4 ppm BBMG, and from at least about 1 ppm BNPD and more preferably from at least about 3 ppm BNPD. Higher concentrations of the active ingredients (e.g., to about 250 ppm BBMG and 150 ppm BNPD) can be used depending on the extent of contamination and the conduciveness of the particular environment to microbial growth. One may use a wide range of ratios of active ingredients, e.g., ratios ranging from about 0.15 parts BBMG to 1 part BNPD to about 40 parts BBMG to 1 part BNPD. More preferred are compositions containing from about 1 part BBMG to 1 part BNPD. Compositions containing the components at a 1 to 1 ratio, 1.64 (i.e. about 2) parts of a preparation containing 25% BBMG (e.g. Tektamer 38) and one part of a preparation containing about 41% BNPD (e.g., Nalco 5780) are especially preferred for use in the instant invention. Those of skill in the art, with the aid of the present disclosure, should be able to determine optimal effective concentrations and ratios to be used for a particular application.

If desired, the synergistic biocides may be formulated together prior to use and delivered as a single reagent. In certain instances, it may be desirable to add solubilizing or emulsifying agents such as surfactants, ethylene glycols, etc., to formulate or emulsify a combined composition. The present inventor has found, for example, that a formulation comprising 4 parts of Tektamer 38 (25% BBMG in a dispersing formula) and 1 part of Nalco 5780 (a 41% solution of BNPD in a solvent containing from about 40-70% and generally about 44% dipropylene glycol monoethyl ether in water) produces a stable dispersion and a formulation suitable for use as part of the present invention. A formulation containing 1 part Nalco 5780 to 2 parts Tektamer 38 is also stable. Similarly, a 1 to 1 mixture of Tektamer 38 and 5780 provides a formulation that is less stable but can be used with agitation to insure suspension of the active ingredients prior to use. Other formulations suitable for convenient storage and delivery of the synergistic biocides of the invention can be prepared according to known formulation technology by those of ordinary skill in the art.

PRACTICAL EXAMPLE

Without limiting the invention in any way, the following example illustrates one method for application of the synergistic biocidal composition in the latex industry. A composition comprising a carboxylated styrene butadiene latex at 25% by weight is mixed with water at 7% by weight, and a trace of a surfactant or dispersant such as CF1885, sold by Chemtex, Charlotte, N.C., and a vicosifier such as Paragum 178 sold by Southern Inc., Simpsonville, S.C., are added with mixing. Ground limestone, e.g., as sold by Frank Glenn Industrial Minerals, Dalton, Ga., in about 66 parts by weight is then compounded with the mixture. To this mixture is added an amount of BBMG and BNPD, (preferably at a ratio of about 1 part of BBMG to 1 part of BNPD) (or, if Tektamer 38 and Nalco 5780 are used, about 1.64 parts of Tektamer 38 to 1 part of compound 5780), effective to produce a biocidal concentration in the mix, e.g. from at least about 0.5 ppm to 250 ppm BBMG and about 0.5 to 150 ppm BNPD. The formulated latex may then be pumped to storage and held until needed and then applied to the carpet backing by any of the number of standard techniques, including for example, spraying, spreading, etc. The processed carpet is rolled to a heat dryer where the latex backing is cured and may be processed further according to standard techniques in the art.

EXPERIMENTAL EXAMPLES

The experimental examples below demonstrate the synergistic activity of BBMG and BNPD in inhibiting microbial growth in latex as measured by a test for biocide assessment. The test is described in co-pending U.S. patent application Ser. No. 07/670,858, filed Mar. 18, 1991, now abandoned by Linda R. Robertson and in U.S. patent application Ser. No. 08/088,050 by Allen R. Syrinek filed Jul. 7, 1993, now U.S. Pat. No. 5,385,605 both of which are incorporated herein by reference.

The test uses a commercially available reduction-oxidation indicator (resazurin) which changes color from purple to pink in the presence of actively respiring microorganisms. The method used in the examples described below actually contained two separate tests: (1) a method for determining minimum inhibitory concentration (MIC) for a single biocide, and (2) a method for demonstrating that the claimed combination of BBMG and BNPD was synergistic. Test 1 used serial dilutions of single microbicide in the presence of nutrient and indicator. Test 2 uses the same principle of test 1, but uses a number of samples containing different concentrations of BBMG and BNPD. The samples are arranged in a grid (i.e., in the wells of a 96-well microtiter culture plate). Usually, the grid contains high concentrations of biocide A on the top going to lower concentrations of biocide A on the bottom; and high concentrations of biocide B on the right going to low concentrations of biocide B on the left. Each biocide is blended with the other over the grid.

To perform the test a nutrient mixture ("solution 1") containing 0.10 g dextrose, 0.80 g nutrient broth (beef extract with peptone), 0.25 g nondairy creamer (Carnation Coffee-Mate TM ), 22 milligrams of resazurin, 0.10 g $KH_2PO_4$, 0.10 g $Na_2HPO_4$, and 100 ml sterile water is prepared. This solution is then mixed with an equal volume of base latex containing a test organism or culture to produce a nutrient/latex medium ("solution 2"). In the experiments discussed below, the latex was obtained from the Goodyear Chemical Company and had not been treated with any anti-microbial compounds. Solution 2 is then used as a diluent for the product to be tested. For example, a stock mixture containing 2000 ppm Tektamer 38 and another stock mixture containing 2000 ppm of Nalco 5780 were prepared in solution 2.

Typically, a serial dilution of the contaminated latex (without biocides) is performed in column 11 of the plate in order to assess the extent of contamination of the latex. Wells in column 11 are filled with 125 microliters of solution 1, then 125 microliters of the contaminated latex is placed in well A11 and 1:2 serial dilutions of the latex mixture into solution 1 are made in the remaining wells of column 11. When this test is performed, well A11 contains the concentration of contaminated latex/solution 1 present in the wells of columns 1-10 and 12. The remaining wells in column 11 contain 1:2 serial dilutions of the contaminated latex solution.

The test to determine the MIC of a single agent is performed in column 12 of a 96-well plate for biocide A and column 1 of the plate for biocide B. A solution containing the desired concentration of biocide A is made by mixing the appropriate volume of the 2000 ppm biocide solution with the appropriate volume of solution 2. A solution containing the desired concentration of biocide B is made similarly. Next, 125 microliters of solution 2 is placed in each well of columns 1 and 12. Then, 125 microliters of the biocide A preparation is added to well A12 and mixed with the latex. A 125 microliter aliquot from well A12 is added to well B12 and mixed. This procedure is repeated down the column until well H12 has been dosed with biocide, and 125 microliters is discarded from well H12. Biocide B is serially diluted in column 1 in a similar manner. The MIC for each biocide is indicated by the lowest concentration of the biocide effective to prevent microbial growth sufficient to cause a color change in the nutrient/latex medium.

In order to test for synergy, the biocides are mixed over a range of ratios and concentrations. Eight channels of a 12 channel Eppendorf pipet are used to place 125 microliters of solution 2 in each well in columns 2-10. The pipet is then rinsed. Eight channels of the pipet are then used to place 125 microliters of a desired concentration of biocide A in each well of column 10. The pipet is then used to make 2-fold serial dilutions from column 10 to column 2. This produces a concentration gradient for biocide A which goes from the starting concentration (in column 10) to a much lower final concentration in the last column used (e.g. in column 2). Now biocide B at 2(X) of a desired concentration (X), is prepared in solution 2 and 125 microliters of this is pipetted into row A of columns 2–10, and mixed with the 125 $\mu$l of latex in the well to give a 1:2 dilution of the biocide and produce a final biocide B concentration of X. Next a 1X solution of biocide B in solution 2 is prepared and 125 microliters is placed into row B of columns 2–10, and mixed to produce a final biocide concentration of 0.5X. This procedure is repeated on rows C-H in columns 2–10 at concentrations of 0.25X, 0.125X, 0.0625X, etc. This procedure also dilutes the concentration of biocide A by 50%.

The plates are sealed with tape and incubated for twentyfour hours at 37° C. The plates are then visually examined and the data reflecting well color changes are recorded. A color change from violet blue to pink is indicative of microbial contamination. The minimum inhibitory concentration (MIC) of each biocide alone, i.e., the lowest concentration at which no color change was observed, is then recorded. Similarly, for the wells containing mixtures, the concentration of first and second biocides in each well where no color change was observed is recorded. Synergy is then calculated as follows is calculated according to the formula:

$$\frac{Qa}{QA} + \frac{Qb}{QB} = X$$

Qa is the quantity of biocide in the admixture;
QA is the MIC of biocide A;
Qb is the quantity of second biocide in the admixture; and
QB is the MIC of biocide B.

The value of X is then determined. If X is less than one, a synergistic composition is present; if X is equal to one, an additive combination is present, and if X is greater than one, an antagonistic composition is present. Understanding of this procedure may be further facilitated by reference to Kull et al., Applied Microbiology 9:538–554 (1961) and to U.S. Pat. No. 4,661,518 issued Apr. 28, 1987 to LaMarre et al.

EXPERIMENTAL EXAMPLE 1

In this example, a mixed wild culture obtained from a batch of contaminated latex was used as the inoculum to produce a starting contamination level of about $10^5$–$10^7$ cells/well. Tektamer 38 (which contains 25% 2-bromo-2-(bromomethyl)glutaronitrile as an active ingredient) and Nalco 5780 (which contains 41% 2-bromo-2-nitropropane-1,3-diol in an aqueous solution with about 44% percent by weight dipropylene glycol monoethyl ether) were used as sources of the active biocides at the concentrations shown in FIG. 1. The results of this experiment are shown in FIG. 1.

In this experiment, synergistic biocidal activity was observed at 0.5 ppm BBMG and 3.28 ppm BNPD, at 1 ppm BBMG and 3.28 ppm BNPD, at 2 ppm BBMG and 3.28 ppm BNPD, at 4 ppm BBMG and 3.28 BNPD, at 8 ppm BBMG and 3.28 ppm BNPD, at 16 ppm BBMG and 3.28 BNPD, at 16 ppm BBMG and 1.64 ppm BNPD, at 31.25 ppm BBMG and 1.64 BNPD, and at 31.25 ppm BBMG and 0.82 ppm BNPD. Therefore in this experiment, synergy was observed over a wide range of BBMG:BNPD ratios, ranging from as little as about 0.15:1 to about 40:1, which corresponds to a range of from about 0.250 parts Tektamer 38 to 1 part Nalco 5780 to about 64 parts Tektamer 38 to 1 part Nalco 5780.

EXPERIMENTAL EXAMPLE 2

In this example, a culture of Pseudomonas aeruginosa (available from the American Type Culture Collection, Rockville, Md., under deposit number 10145) was used as the inoculum. An aliquot of the seed culture was added to a latex nutrient mixture to produce a bacterial level of about $10^5$–$10^7$ cells/well and tested as described above. Tektamer 38 and Nalco 5780 were used as biocides. The results of this experiment are shown in FIG. 2.

In this experiment, synergistic biocidal activity was observed at 2 ppm BBMG and 1.64 ppm BNPD, and at 4 ppm BBMG and 0.82 ppm BNPD. Therefore in this experiment, synergy was observed over a wide range of BBMG:BNPD ratios, ranging from as little as about 1:1 to about 5:1, which corresponds to a range of from about 2 parts Tektamer 38 to 1 part Nalco 5780 to about 8 parts Tektamer 38 to 1 part Nalco 5780.

EXPERIMENTAL EXAMPLE 3

In this example, a culture of Pseudomonas aeruginosa (available from the American Type Culture Collection, Rockville, Md., under deposit number 10145) was used as the inoculum. An aliquot of the seed culture was added to a latex nutrient mixture to produce a bacterial level of about $10^5$–$10^7$ cells/well and tested as described above. Tektamer 38 and Nalco 5780 were used as biocides. The results of this experiment are shown in FIG. 3.

In this experiment, synergistic biocidal activity was observed at 1 ppm BBMG and 3.28 ppm BNPD, at 2 ppm BBMG and 3.28 ppm BNPD, at 4 ppm BBMG and 3.28 ppm BNPD, at 8 ppm BBMG and 3.28 BNPD, and at 16 ppm BBMG and 1.64 ppm BNPD. Therefore in this experiment, synergy was observed over a wide range of BBMG:BNPD ratios, ranging from as little as 3:1 to 10:1, which corresponds to a range of from about 0.5 part Tektamer 38 to 1 part Nalco 5780 to about 16 parts Tektamer 38 to 1 part Nalco 5780.

EXPERIMENTAL EXAMPLE 4

In this experiment a wild culture was used as inoculum (about $10^5$–$10^7$ cells/well) and Tektamer 38 and Nalco 5780 were used as biocides.

In this experiment, synergistic biocidal activity was observed at 16 ppm BBMG and 3.28 ppm BNPD, and at 31.25 ppm BBMG and 1.64 ppm BNPD. Therefore in this experiment, synergy was observed over a wide range of BBMG:BNPD ratios, ranging from as little as about 5:1 to 20:1, which corresponds to a range of from about 8 parts Tektamer 38 to 1 part Nalco 5780 to about 33 parts Tektamer 38 to 1 part Nalco 5780.

The foregoing description of the invention has been directed to particular preferred embodiments in accordance with the requirements of the patent statutes and for purposes of explanation and illustration. It will be apparent, however, to those skilled in the art that many modifications and changes may be made without departing from the scope and the spirit of the invention.

For example, numerous methods for formulating and using the synergistic anti-microbial agents may be used.

In addition, the anti-microbial agents may be used in a wide variety of applications not specifically mentioned here. It is apparent that the invention may also be utilized, with suitable modifications within the state of the art. It is the Applicant's intention in the following claims to cover all such equivalent modifications and variations which fall within the true spirit and scope of the invention.

What is claimed is:

1. An anti-microbial composition comprising synergistic effective amounts of 2-bromo-2-(bromomethyl)-glutaronitrile and 2-bromo-2-nitro-propane-1,3-diol in a ratio ranging from 0.15 parts 2-bromo-2-(bromomethyl)glutaronitrile to 1 part 2-bromo-2-nitro-propane-1,3-diol to 40 parts 2-bromo-2-(bromomethyl)-glutaronitrile to 1 part 2-bromo-2-nitro-propane-1,3-diol.

2. The composition of claim 1 wherein the composition contains at least about 0.5 parts per million 2-bromo-2-(bromomethyl)glutaronitrile and at least 1.64 parts per million 2-bromo-2-nitro-propane-1,3-diol.

3. The composition of claim 1 wherein composition contains at least about 0.4 parts per million 2-bromo-2-(bromomethyl)glutaronitrile and at least 1 parts per million 2-bromo-2-nitro-propane-1,3-diol.

4. The composition of claim 1 wherein the composition contains at least about 16 parts per million 2-bromo-2-(bromomethyl)glutaronitrile and at least 3 parts per million 2-bromo-2-nitro-propane-1,3-diol.

5. An anti-microbial formulation comprising synergistic effective amounts of between 1 and 4 parts of a formulated dispersion of about 25% 2-bromo-2-(bromomethyl)-glutaronitrile to about one part of solution containing about 41% 2-bromo-2-nitro-propane-1,3-diol.

6. The formulation of claim 5 wherein the ratio of said dispersion to said solution is about 2 parts to 1 part.

7. The formulation of claim 5 wherein said emulsion comprises about 25% 2-bromo-2-(bromomethyl)-glutaronitrile in formulated dispersion.

8. The formulation of claim 5 wherein said solution comprises dipropylene glycol monoethyl ether and about 41% 2-bromo-2-nitro-propane-1,3-diol.

9. A method for inhibiting microbial growth in a composition that contains a latex comprising adding to the composition 2-bromo-2-(bromomethyl)-glutaronitrile and 2-bromo-2-nitro-propane-1,3-diol in a ratio ranging from about 0.15 parts to 1 part 2-bromo-2-nitro-propane-1,3-diol to 40 parts 2-bromo-2-(bromomethyl)-glutaronitrile to 1 part 2-bromo-2-nitro-propane-1,3-diol in synergistic effective amounts of each which in combination, are effective to inhibit microbial growth.

10. The method of claim 9 wherein the amount of 2-bromo-2-(bromomethyl)-glutaronitrile is at least about 0.5 parts per million and the amount of 2-bromo-2-nitro-propane-1,3-diol is at least about 1.64 parts per million.

11. The method of claim 9 wherein the amount of 2-bromo-2-(bromomethyl)-glutaronitrile is at least about 0.4 parts per million and the amount of 2-bromo-2-nitro-propane-1,3-diol is at least about 1 part per million.

12. The method of claim 9 wherein the amount of 2-bromo-2-(bromomethyl)-glutaronitrile is at least about 16 parts per million and the amount of 2-bromo-2-nitro-propane-1,3-diol is at least about 3 parts per million.

13. The method of claim 9 wherein said latex composition is an uncured latex compound formulated for use as a carpet backing or adhesive.

14. Method of claim 9 wherein said latex composition is an uncured latex composition formulated for use as a paper coating.

15. A composition for use as a carpet backing comprising:
a) latex;
b) water;
c) a filling agent; and
d) 2-bromo-2-(bromomethyl)-glutaronitrile and 2-bromo-2-nitro-propane-1,3-diol in synergistic effective amounts of each, which in combination, are effective to inhibit microbial growth in said latex.

* * * * *